(12) United States Patent
Iwao et al.

(10) Patent No.: US 8,703,178 B2
(45) Date of Patent: *Apr. 22, 2014

(54) PERCUTANEOUS ADMINISTRATION DEVICE OF BISOPROLOL

(75) Inventors: Yoshihiro Iwao, Ibaraki (JP); Kensuke Matsuoka, Ibaraki (JP); Katsuhiro Okada, Ibaraki (JP); Kunihiro Minami, Fukushima (JP); Shuichiro Yuasa, Fukushima (JP)

(73) Assignees: Nitto Denko Corporation, Osaka (JP); Toa Eiyo Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/528,194

(22) PCT Filed: Mar. 6, 2008

(86) PCT No.: PCT/JP2008/054022
§ 371 (c)(1),
(2), (4) Date: Aug. 21, 2009

(87) PCT Pub. No.: WO2008/108424
PCT Pub. Date: Sep. 12, 2008

(65) Prior Publication Data
US 2010/0098747 A1    Apr. 22, 2010

(30) Foreign Application Priority Data
Mar. 8, 2007    (JP) .................. 2007-059279

(51) Int. Cl.
*A61K 9/70*     (2006.01)
*A61K 31/138*   (2006.01)
*A61P 9/00*     (2006.01)

(52) U.S. Cl.
USPC .......................................... 424/449; 514/652

(58) Field of Classification Search
None
See application file for complete search history.

(56) References Cited

U.S. PATENT DOCUMENTS

| | | | |
|---|---|---|---|
| 5,149,719 A | | 9/1992 | Ferber et al. |
| 5,508,038 A | * | 4/1996 | Wang et al. ............... 424/448 |
| 6,117,447 A | | 9/2000 | Nakano et al. |
| 6,303,141 B1 | | 10/2001 | Fischer et al. |
| 6,486,147 B2 | | 11/2002 | Baldo et al. |
| 7,029,693 B2 | | 4/2006 | Hori et al. |
| 7,250,546 B2 | | 7/2007 | Tsuruda et al. |
| 2003/0109819 A1 | | 6/2003 | Tsuruda et al. |
| 2004/0142024 A1 | | 7/2004 | Chono et al. |
| 2006/0078604 A1 | * | 4/2006 | Kanios et al. .............. 424/449 |
| 2006/0240086 A1 | | 10/2006 | Tateishi et al. |
| 2007/0083139 A1 | | 4/2007 | Tsuruda et al. |
| 2009/0012181 A1 | | 1/2009 | Amano et al. |
| 2009/0169603 A1 | | 7/2009 | Iwao et al. |
| 2009/0291126 A1 | | 11/2009 | Iwao et al. |
| 2010/0098747 A1 | | 4/2010 | Iwao et al. |
| 2010/0227932 A1 | | 9/2010 | Satoshi-Amano et al. |

FOREIGN PATENT DOCUMENTS

| | | |
|---|---|---|
| CA | 2 583 340 A1 | 4/2006 |
| CO | 0821712 | 2/2008 |
| EP | 1188436 A2 | 3/2002 |
| EP | 1652508 A1 * | 5/2006 |
| JP | 03-127727 A | 5/1991 |
| JP | 04-055487 | 2/1992 |
| JP | 06-145626 | 5/1994 |
| JP | 07-330591 | 12/1995 |
| JP | 09-511987 A | 12/1997 |
| JP | 10-152434 A | 6/1998 |
| JP | 11-029496 A | 2/1999 |
| JP | 11-502827 A | 3/1999 |
| JP | 2002-038114 | 2/2002 |
| JP | 2002-080349 A | 3/2002 |
| JP | 2002-187836 A | 7/2002 |
| JP | 2003-313122 A | 11/2003 |
| JP | 2003313122 A * | 11/2003 |
| JP | 2004-502725 A | 1/2004 |
| JP | 2004-244585 | 9/2004 |
| JP | 2006-76994 A | 3/2006 |
| JP | 2006-225319 A | 8/2006 |
| JP | 2005-023088 A | 1/2007 |
| KR | 10-2008-0077404 A | 8/2008 |
| KR | 10-1246400 B1 | 3/2013 |
| MX | 2008003328 A | 7/2008 |
| WO | 01-43729 A1 | 6/2001 |
| WO | 01/43729 A1 | 6/2001 |

(Continued)

OTHER PUBLICATIONS

Tan et al. Pressure-sensitive adhesives for transdermal drug delivery systems. PSTT vol. 2, No. 2, pp. 60-69 (Feb. 1999).*
First Office Action issued Oct. 27, 2010, in counterpart Chinese Application No. 200880007650.1.
International Search Report for PCT/JP2008/054022 dated Apr. 15, 2008.
Russian Office Action issued on May 27, 2011 in the corresponding Russian Patent Application No. 2009137122.
Office Action dated Jul. 22, 2011 from the State Intellectual Property Office of the People's Republic of China in counterpart Chinese application No. 200880007650.1.

(Continued)

*Primary Examiner* — Daniel Sullivan
*Assistant Examiner* — Peter Anthopolos
(74) *Attorney, Agent, or Firm* — Sughrue Mion, PLLC (57) ABSTRACT

The present invention relates to a percutaneous administration device of bisoprolol, which includes a backing; and a pressure-sensitive adhesive layer containing bisoprolol, which is laminated on one surface of the backing, wherein the maximum value of a release rate of bisoprolol during a period of from immediately after the application on skin until a lapse of 24 hours is 30 μg/cm$^2$/hr or less; and wherein the release rate of bisoprolol at the time of a lapse of 24 hours after the application on skin is 10 μg/cm$^2$/hr or less. The percutaneous administration device of the present invention is reduced in the skin irritation during the application, especially at the time of peeling, and is capable of persistently administrating a therapeutically or preventively effective amount of bisoprolol into a living body.

18 Claims, 3 Drawing Sheets

(56) References Cited

FOREIGN PATENT DOCUMENTS

| WO | 02-03969 A2 | 1/2002 |
|---|---|---|
| WO | 2005-011662 A1 | 2/2005 |
| WO | 2005/011662 A1 | 2/2005 |
| WO | 2005/072716 A1 | 8/2005 |
| WO | 2006/044206 A3 | 4/2006 |
| WO | 2006-080199 A1 | 8/2006 |
| WO | WO 2006080199 A1 * | 8/2006 |
| WO | 2007-029781 A1 | 3/2007 |
| WO | 2007-069661 A1 | 6/2007 |

OTHER PUBLICATIONS

Communication, dated Nov. 2, 2011, issued by the State Intellectual Property Office of P.R. China in corresponding Chinese Application No. 200880007650.1.
Office Action issued Mar. 28, 2012 in corresponding Chinese application No. 200880007650.1.
Communication, dated Sep. 27, 2011, issued by the Israeli Patent Office in corresponding Israeli Application No. 200378.
Office Action dated Sep. 25, 2012 issued by the Australian Patent Office in counterpart Australian Application No. 2008221861.
Office Action dated Sep. 9, 2012 issued by the Japanese Patent Office in counterpart Japanese Application No. 2008-057691.
Communication dated May 10, 2012 from the Australian Patent Office in counterpart Australian application No. 2008221861.
Extended European Search Report issued Jun. 3, 2013, in related European Patent Application No. 08721442.5.
Office Action dated Aug. 14, 2012 issued by the Colombia Patent Office in counterpart Colombian Application No. 09-95795.
Office Action dated Sep. 24, 2012 issued by the Taiwanese Patent Office in counterpart Taiwanese Application No. 01176/10121004810.
Office Action issued Sep. 8, 2011, in Chinese Application No. 200680046916.4.
Office Action issued Dec. 13, 2011, in Japanese Patent Application No. 2006-328922.
Office Action issued Dec. 23, 2008, in European Patent Application No. 06783221.2.
VISTANEX PIB General Information; 2008; two (2) pages total.
Extended European Search Report issued Oct. 29, 2008 in corresponding European Patent Application No. 06783221.2.
Houng Jin Choi, et al.; "Relaxation Time of Polymer Solutions From Rod-Climbing Height (Part 2)"; Korean Journal o Chem. Eng.; vol. 9 No. 2; May 1, 1992; pp. 74-82.
Office Action issued Feb. 29, 2012, in corresponding Columbian Patent Application No. PCT/08-21712.
Office Action issued Feb. 28, 2012 in corresponding Japanese Patent Application No. 2006-235270.
Office Action issued Feb. 7, 2012 in corresponding Taiwanese Patent Application No. 095133239.
Office Action issued Mar. 5, 2012 in corresponding Canadian Patent Application No. 2,621,867.
Office Action issued Nov. 10, 2011, in Columbian Patent Application No. 08-021712.
Office Action issued Oct. 5, 2011, in corresponding Japanese Patent Application No. 2006-235270.
Office Action issued Nov. 22, 2010, in corresponding Australian Patent Application No. 2006288260.
Extended European Search Report issued Jun. 15, 2012, in corresponding European Patent Application No. 06834629.5.
Extended European Search Report issued Jul. 22, 2011 in corresponding Application No. 11003489.9.
Chinese Office Action issued May 25, 2011, in corresponding Application No. 200680033186.4.
Mexican Office Action issued Jun. 2, 2011, in corresponding Application No. MX/a/2008/003328.
Japanese Information Offer Form dated Apr. 15, 2009.
Korean Office Action issued Jul. 10, 2012, in corresponding Application No. 10-2008-7005702.
Taiwanese Office Action issued Jul. 27, 2012, in corresponding Application No. 095133239.
Columbian Office Action issued Nov. 26, 2012 in corresponding Application No. PCT/08-021712.
European Office Action issued Jan. 28, 2013, in counterpart European application No. 11003489.9.
Chinese Office Action issued Sep. 28, 2012, in corresponding Application No. 200680033186.4.
Canadian Office Action issued Jul. 3, 2012, in corresponding Application No. 2633125.
International Search Report issued Mar. 20, 2007, in corresponding International Application No. PCT/JP2006/324874.
Non-final Office Action issued Dec. 15, 2010, in corresponding U.S. Appl. No. 12/066,095.
Final Office Action issued May 20, 2011, in corresponding U.S. Appl. No. 12/066,095.
Advisory Action issued Aug. 25, 2011, in corresponding U.S. Appl. No. 12/066,095.
Final Office Action issued Jul. 29, 2011, in corresponding U.S. Appl. No. 12/097,260 (US Patent No. 8,298,572).
Non-Final Office Action issued Sep. 15, 2010, in corresponding U.S. Appl. No. 12/097,260 (US Patent No. 8,298,572).
Non-Final Office Action issued Feb. 18, 2011, in corresponding U.S. Appl. No. 12/097,260 (US Patent No. 8,298,572).
Non-Final Office Action issued Dec. 16, 2011, in corresponding U.S. Appl. No. 12/097,260 (US Patent No. 8,298,572).
Office Action dated May 10, 2013 issued by the Canadian Intellectual Property Office in corresponding Canadian Patent Application No. 2,678,424.
Communication issued Mar. 22, 2013, by the Indian Patent Office in related Application No. 1166/CHENP/2008.
Office Action, dated Mar. 13, 2013, issued by the Korean Patent Office in counterpart Korean Patent Application No. 10-2008-7016978.
Office Action, dated Feb. 25, 2013, issued by the Colombian Patent Office in counterpart Colombian Application No. 09-095795.
Office Action, dated Feb. 27, 2013, issued by the Taiwanese Patent Office in counterpart Taiwanese Application No. 097108005.
Office Action, dated Mar. 5, 2013, issued by the Japanese Patent Office in counterpart Japanese Application No. 2008-057691.
Office Action, dated Mar. 18, 2013, issued by the Israeli Patent Office in counterpart Israeli Application No. 200378.
Office Action, dated Jun. 19, 2013, issued by the Mexican Patent Office in counterpart Mexican Application No. MX/a/2009/008933.
Communication dated Sep. 17, 2013 issued by the Korean Intellectual Property Office in counterpart Korean Patent Application No. 10-2009-7018633.
Communication dated Aug. 19, 2013 issued by the Japanese Patent Office in Japanese Patent Application No. 2012-120476, which corresponds to U.S. Appl. No. 12/066,095.
Hearing Notice issued on Jan. 21, 2014, in corresponding Indian application No. 166/CHENP/2008.

* cited by examiner

PERCUTANEOUS ADMINISTRATION DEVICE OF BISOPROLOL

TECHNICAL FIELD

The present invention relates to a percutaneous administration device of bisoprolol, which is capable of administering bisoprolol from a skin surface into a body.

BACKGROUND ART

Bisoprolol which is a highly selective antagonist (β-blocker) of a $β_1$-receptor of sympathetic nerve has been used for improving essential hypertension, angina pectoris and arrhythmia, and a fumarate thereof is orally administered as a tablet. On the other hand, in the case of oral administration, there are encountered problems that the sustention of the effects of bisoprolol is not sufficient; and that the concentration thereof in blood which is more than necessary is temporarily found after the administration, whereby side effects easily occur. In order to improve these problems, a percutaneous administration device has been desired.

In β-blockers, although various oral agents have been developed so far, reports on side effects such as irritation on a gastrointestinal mucosa have not been found in the oral administration. However, in view of the fact that the skin irritation which is characteristic to the drug occurs in the drug administration route through a skin, it was very difficult from the viewpoint of practical use to choose them as a drug for percutaneous absorption preparation. As to bisoprolol which is a β-blocker, there was also a possibility that when formed in a percutaneous absorption preparation, the skin irritation is revealed by the drug.

Although a bisoprolol-containing patch is described in, for example, Patent Documents 1 and 2, investigations have been made with focusing on stably keeping the concentration in blood, and it is hard to say that its skin irritation is thoroughly investigated.

Furthermore, as to such a bisoprolol-containing patch, repeated application is desired for the purpose of obtaining a sufficient therapeutic or preventive effect. In these patent documents, the repeated administration for repeating peeling and application every 24 hours is supposed. However, in such a patch, since a maximum value of human skin permeation rate exceeds 30 μg/cm²/hr, there is a high possibility that strong skin irritation by bisoprolol is generated depending upon a patient. As has been described, a percutaneous administration device in which the skin irritation during the application, especially at the time of peeling is thoroughly reduced and by which a therapeutically or preventively effective amount of bisoprolol can be persistently administered into a living body has not been known yet.
Patent Document 1: WO 2005/011662
Patent Document 2: WO 2006/080199

DISCLOSURE OF THE INVENTION

The invention has been made in view of the foregoing problems, and the propose of the invention is to provide a percutaneous administration device in which the skin irritation during the application, especially at the time of peeling is reduced and by which a therapeutically or preventively effective amount of bisoprolol can be persistently administered into a living body.

In order to solve the foregoing problems, the present inventors made extensive and intensive investigations, and as a result, they found that it is effective as a measure for suppressing the skin irritation of bisoprolol to control an absolute amount of skin permeation rate of bisoprolol. Then, the present inventors further made investigations in detail. As a result, it has been found that by controlling a maximum value of a release rate of bisoprolol during a period of from immediately after the application on skin until a lapse of 24 hours and a release rate of bisoprolol at the time of a lapse of 24 hours after the application on skin within the specified ranges, respectively, not only the skin irritation can be reduced, but a new effect which is effective for therapy or prevention can be exerted, leading to accomplishment of the invention.

Specifically, the invention relates to the following (1) to (5).
(1) A percutaneous administration device of bisoprolol, which comprises:
  a backing; and
  a pressure-sensitive adhesive layer containing bisoprolol, which is laminated on one surface of the backing,
  wherein the maximum value of a release rate of bisoprolol during a period of from immediately after the application on skin until a lapse of 24 hours is 30 μg/cm²/hr or less; and
  wherein the release rate of bisoprolol at the time of a lapse of 24 hours after the application on skin is 10 μg/cm²/hr or less.
(2) The percutaneous administration device according to (1), wherein an absolute value of an inclination of reduction of the release rate of bisoprolol is 1.25 or less.
(3) The percutaneous administration device according to (1) or (2), wherein the maximum value of the release rate of bisoprolol is obtained at a time during a period of from immediately after the application on skin until a lapse of 6 hours.
(4) The percutaneous administration device according to any one of (1) to (3), wherein an availability of bisoprolol during a period of from immediately after the application on skin until a lapse of 24 hours is 65% by weight or more.
(5) The percutaneous administration device according to any one of (1) to (4), wherein an accumulated release amount of bisoprolol during a period of from immediately after the application on skin until a lapse of 12 hours is larger than an accumulated release amount of bisoprolol during a period of from a lapse of 12 hours until a lapse of 24 hours after the application on skin.

Since the percutaneous administration device of bisoprolol of the invention operates such that a maximum value of a release rate of bisoprolol during a period of from immediately after the application on skin until a lapse of 24 hours is 30 μg/cm²/hr or less, not only the skin irritation by bisoprolol is suppressed, but the possibility of side effects such as bradycardia and vertigo to be caused due to excessive depression is eliminated, whereby sufficient safety is secured.

Furthermore, at the time of peeling of the percutaneous administration device of bisoprolol, for example, at the time of reapplication, physical irritation due to the peeling is combined with skin irritation of the drug, namely bisoprolol itself, whereby strong skin irritation tends to be generated. It is supposed that this is because at the time of peeling of the percutaneous administration device of bisoprolol, the skin irritation is generated by both physical irritation due to an adhesion strength of the pressure-sensitive adhesive layer and chemical irritation due to bisoprolol itself.

On the other hand, since the percutaneous administration device of bisoprolol of the invention operates such that a release rate of bisoprolol at the time of a lapse of 24 hours after the application on skin is 10 μg/cm²/hr or less, the skin irritation due to bisoprolol itself at the time of peeling is hardly generated. Furthermore, bisoprolol in the pressure-sensitive adhesive layer is already thoroughly released at the time of peeling, and bisoprolol does not remain so much in the pressure-sensitive adhesive layer. Therefore, coagulation properties of the pressure-sensitive adhesive layer are improved, and the physical skin irritation at the time of peeling is low.

Furthermore, in particular, the percutaneous administration device of bisoprolol of the invention may operate such that the maximum value of release rate of bisoprolol is obtained at a time during a period of from immediately after the application on skin until a lapse of 6 hours. Therefore, in that case, since the release rate of bisoprolol is thoroughly reduced at the time of peeling, the skin irritation of bisoprolol itself is hardly generated. Thus, according to the percutaneous administration device of bisoprolol of the invention, the skin irritation is thoroughly reduced. In addition, in the percutaneous administration device of the invention, not only the therapy with an immediate effect becomes possible, but since a peak of the concentration of bisoprolol in blood is slightly delayed in terms of time as compared with a peak of the release rate of bisoprolol, when the percutaneous administration device of the invention is applied before sleeping, a depression effect is exhibited at maximum at the time of wake-up in which the depression effect is most demanded.

Moreover, according to the percutaneous administration device of bisoprolol of the invention, when an absolute value of an inclination of reduction of the release rate of bisoprolol is controlled to be 1.25 or less, the reduction of the release rate of bisoprolol becomes gentle, and a large fluctuation of the release rate of bisoprolol is suppressed. Therefore, it is possible to stably release a therapeutically or preventively effective amount of bisoprolol. As a result, it is possible to sustain the concentration of bisoprolol in blood substantially constantly over a long period of time, and the skin irritation accompanied with the fluctuation is reduced. Therefore, the skin irritation during the application is much more reduced.

DESCRIPTION OF REFERENCE NUMERALS AND SIGNS

1: Backing
2: Pressure-sensitive adhesive layer
3: Peel-off liner
10: Percutaneous administration device of bisoprolol

BEST MODE FOR CARRYING OUT THE INVENTION

The invention is hereunder described in detail with reference to preferred embodiments thereof. In the description of the drawings, the same element is given the same symbol, and its overlapping explanation is omitted. For the sake of convenience for illustration, a dimensional ratio on the drawing is not always consistent with that in the explanation.

Figure 1:
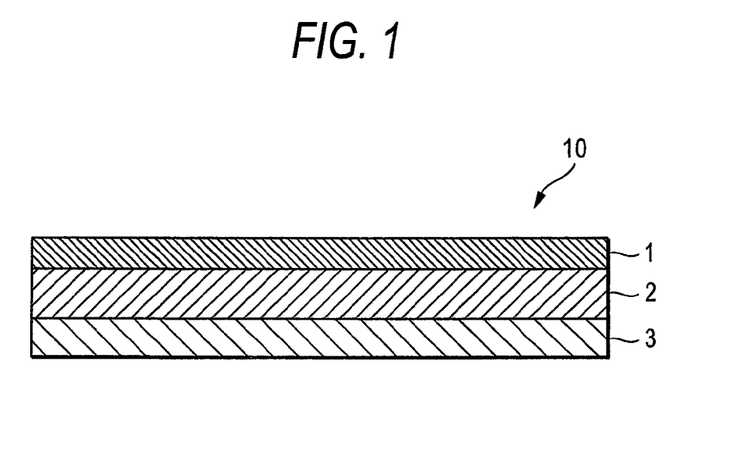
FIG. 1 is a cross-sectional view illustrating one embodiment of the percutaneous administration device of bisoprolol of the invention.

FIG. 1 is a cross-sectional view illustrating one embodiment of a percutaneous administration device of bisoprolol of the invention (hereinafter also referred to simply as "percutaneous administration device"). In this embodiment, a percutaneous administration device 10 is provided with a backing 1, a pressure-sensitive adhesive layer 2 laminated on one surface of the backing 1 and a peel-off liner 3 laminated on the surface of the pressure-sensitive adhesive layer 2.

The pressure-sensitive adhesive layer 2 contains bisoprolol, and operates such that a maximum value of a release rate of bisoprolol during a period of from immediately after the application on skin until a lapse of 24 hours is 30 $\mu g/cm^2/hr$ or less and that a release rate of bisoprolol at the time of a lapse of 24 hours after the application on skin is 10 $\mu g/cm^2/hr$ or less.

The release rate of bisoprolol ($\mu g/cm^2/hr$) as referred to herein is a value obtained by converting the release amount of bisoprolol per unit area of the surface to be applied on skin of the pressure-sensitive adhesive layer into one per unit time, and it refers to a human skin permeation rate obtained by measuring a skin permeation rate of bisoprolol on a mouse skin in vitro and simulating it by a computation software for skin permeation rate. Concretely, it refers to that measured in accordance with a method described in the Test Method of the Examples of the present specification.

Bisoprolol is already marketed as an oral drug, and in the case of a tablet, bisoprolol is contained in a form of an acid salt such as bisoprolol fumarate. In the invention, bisoprolol includes not only bisoprolol in a free form (free base) but pharmaceutically acceptable salts thereof. Accordingly, in the invention, although bisoprolol can be contained in a salt form in the pressure-sensitive adhesive layer, bisoprolol in a salt form is lower in the skin permeability than bisoprolol in a free form, and therefore, it is desirable that bisoprolol in a free form having much higher skin permeability is contained in the pressure-sensitive adhesive layer.

According to the percutaneous administration device of the invention, a maximum value of a release rate of bisoprolol during a period of from immediately after the application on skin until a lapse of 24 hours is 30 $\mu g/cm^2/hr$ or less. When it exceeds 30 $\mu g/cm^2/hr$, the skin irritation by bisoprolol is generated. From this viewpoint, it is desirable that the maximum value of release rate of bisoprolol during a period of from immediately after the application on skin until a lapse of 24 hours is preferably 27.5 $\mu g/cm^2/hr$ or less, more preferably 25 $\mu g/cm^2/hr$ or less, further preferably 22.5 $\mu g/cm^2/hr$ or less, and most preferably 20 $\mu g/cm^2/hr$ or less. In the invention, the smaller the maximum value of release rate of bisoprolol during a period of from immediately after the application on skin until a lapse of 24 hours is, the more the effect for reducing the skin irritation is achieved. However, when the maximum value thereof is too small, it is necessary to make the area of the percutaneous administration device extremely large for the purpose of securing an effective dose for therapy or prevention. As a result, there is a possibility that the stress of a patient during the application becomes large. Further, there is also a possibility that practicality such as handing properties is reduced. From these viewpoints, it is possible to set up a lower limit of the maximum value of release rate of bisoprolol during a period of from immediately after the application on skin until a lapse of 24 hours preferably at 5 $\mu g/cm^2/hr$, and more preferably at 7.5 $\mu g/cm^2/hr$.

Although a method for controlling the maximum value of release rate of bisoprolol at 30 $\mu g/cm^2/hr$ or less is not particularly limited, it can be, for example, achieved as follows.

In the pressure-sensitive adhesive layer, for example, bisoprolol is contained in an amount of from 0.5 to 5% by weight, preferably from 0.5 to 4% by weight, and more preferably from 0.5 to 3% by weight on the basis of the total weight of the pressure-sensitive adhesive layer. When it is less than 0.5% by weight, there is a possibility that the maximum value of release rate of bisoprolol falls below 5 μg/cm$^2$/hr, whereas when it exceeds 5% by weight, there is a possibility that the maximum value of release rate of bisoprolol exceeds 30 μg/cm$^2$/hr.

In such a way, by making the proportion of the drug relative to the total weight of the pressure-sensitive adhesive layer fall within the foregoing range, a desired maximum value of the release rate of bisoprolol during a period of from immediately after the application on skin until a lapse of 24 hours can be efficiently obtained.

Furthermore, according to the percutaneous administration device of the invention, a release rate of bisoprolol at the time of a lapse of 24 hours after the application on skin is 10 μg/cm$^2$/hr or less. When it exceeds 10 μg/cm$^2$/hr, the skin irritation of bisoprolol at the time of peeling-off remains. From this viewpoint, it is desirable that an upper limit of the release rate of bisoprolol at the time of a lapse of 24 hours after the application on skin is preferably 8 μg/cm$^2$/hr, and more preferably 6 μg/cm$^2$/hr. In the invention, the smaller the release rate of bisoprolol at the time of a lapse of 24 hours after the application on skin, the more the effect for reducing the skin irritation at the time of peeling is achieved. However, when the release rate is too small, it is necessary to make the area of the percutaneous administration device extremely large for the purpose of assuring an effective dose for therapy or prevention. As a result, there is a possibility that the stress of a patient during the application becomes large. Further, there is also a possibility that practicality such as handing properties is reduced. From these viewpoints, although a lower limit of the release rate of bisoprolol at the time of a lapse of 24 hours after the application on skin may be 0 μg/cm$^2$/hr, it is possible to set up the lower limit thereof preferably at 1 μg/cm$^2$/hr, and more preferably at 2 μg/cm$^2$/hr.

Although a method for controlling the release rate of bisoprolol at the time of a lapse of 24 hours after the application on skin at 10 μg/cm$^2$/hr or less is not particularly limited, it can be, for example, achieved as follows. In the pressure-sensitive adhesive layer, for example, bisoprolol is contained in an amount of from 0.1 to 0.7 mg/cm$^2$, preferably from 0.1 to 0.6 mg/cm$^2$, and more preferably from 0.1 to 0.5 mg/cm$^2$. When it is less than 0.1 mg/cm$^2$, there is a possibility that bisoprolol in the pressure-sensitive adhesive layer transfers into the skin before a lapse of 24 hours, whereby it becomes difficult to reveal persistent medicinal effects, whereas when it exceeds 0.7 mg/cm$^2$, there is a possibility that the release rate of bisoprolol at the time of a lapse of 24 hours after the application on skin exceeds 10 μg/cm$^2$/hr.

In such a way, by making the content of bisoprolol per unit area, which is contained in the pressure-sensitive adhesive layer, fall within the prescribed range, it is possible to efficiently control the release rate of bisoprolol at the time of a lapse of 24 hours after the application on skin within the foregoing range.

Furthermore, in the percutaneous administration device of the invention, an absolute value of an inclination of reduction of the release rate of bisoprolol is preferably 1.25 or less. From the viewpoint of suppressing a fluctuation of the release rate of bisoprolol, it is desirable that the absolute value of an inclination of reduction is more preferably 1.1 or less, further preferably 1.0 or less, even further preferably 0.8 or less, and most preferably 0.7 or less. When the absolute value of an inclination of reduction exceeds 1.25, it tends to be difficult to stably release a therapeutically or preventively effective amount of bisoprolol, and side effects such as bradycardia and vertigo to be caused due to depression which is caused following a fluctuation of the concentration in blood easily reveal, and the skin irritation is easily generated. From the viewpoint of persistently administering a therapeutically or preventively effective amount of bisoprolol into a living body, it is preferable that a lower limit of the absolute value of an inclination of reduction is as small as possible, and it is preferably 0. Indeed, from the viewpoint of controlling the release rate of bisoprolol at the time of a lapse of 24 hours after the application on skin at 10 μg/cm$^2$/hr or less, the lower limit thereof is preferably 0.1, more preferably 0.2, and further preferably 0.3.

The inclination of reduction of the release rate of bisoprolol as referred to in the invention refers to a degree of change with time of the release rate of bisoprolol during a period of from after it has reached a maximum value of a release rate of bisoprolol until a lapse of 24 hours and means a value determined according to the following equation (1).

$$\text{Inclination of reduction of the release rate of bisoprolol (μg/cm}^2\cdot\text{hr}^2) = (y_2-y_1)/(x_2-x_1) \tag{1}$$

$x_1$: Time at which the release rate of bisoprolol arrives at a maximum value during a period of from after the application on skin until a lapse of 24 hours (hr).

$x_2$: 24 (hr)

$y_1$: Maximum value of the release rate of bisoprolol during a period of from after the application on skin until a lapse of 24 hours (μg/cm$^2$/hr).

$y_2$: Release rate of bisoprolol at the time of a lapse of 24 hours after the application on skin (μg/cm$^2$/hr).

A method for controlling the inclination of reduction of the release rate of bisoprolol at 1.25 or less is not particularly limited, and examples thereof include a method in which not only a proportion of bisoprolol relative to the total weight of the pressure-sensitive adhesive layer is set to fall within the foregoing range, but the content of bisoprolol per unit area, which is contained in the pressure-sensitive adhesive layer, is also set to fall within the foregoing range. In such a way, when the proportion and the content per unit area of bisoprolol, which is contained in the pressure-sensitive adhesive layer, are set to fall within the prescribed ranges, respectively, a large fluctuation of the release rate of bisoprolol is suppressed. As a result, a therapeutically or preventively effective amount of bisoprolol can be persistently administered into a living body, and the skin irritation during the application is much more reduced.

The pressure-sensitive adhesive to be used for forming the pressure-sensitive adhesive layer is not particularly limited, and examples thereof include acrylic pressure-sensitive adhesives composed of an acrylic polymer; rubber based pressure-sensitive adhesives such as styrene/diene/styrene block copolymers (for example, a styrene/isoprene/styrene block copolymer and a styrene/butadiene/styrene block copolymer), polyisoprene, polyisobutylene, butyl rubber and polybutadiene; silicone based pressure-sensitive adhesives such as silicone rubbers, dimethylsiloxane bases and diphenylsiloxane bases; vinyl ether based pressure-sensitive adhesives such as polyvinyl methyl ether, polyvinyl ethyl ether and polyvinyl isobutyl ether; vinyl ester based pressure-sensitive adhesives such as a vinyl acetate/ethylene copolymer; and polyester based pressure-sensitive adhesives composed of a carboxylic acid component (for example, dimethyl terephthalate, dimethyl isophthalate and dimethyl phthalate) and a polyhydric alcohol component (for example, ethylene glycol). From the viewpoint of skin adhesiveness, a hydrophobic pressure-sensitive adhesive is preferable, and a non-hydrous pressure-sensitive adhesive layer is preferable.

Acrylic pressure-sensitive adhesives are preferable from the viewpoints of moisture permeability and drug solubility. For the purpose of imparting sufficient skin adhesiveness to the pressure-sensitive adhesive layer, the acrylic pressure-sensitive adhesive is preferably contained in an amount of from 30 to 75% by weight, more preferably from 35 to 70% by weight, and further preferably from 40 to 65% by weight relative to the total weight of the pressure-sensitive adhesive layer.

Examples of the acrylic pressure-sensitive adhesive include acrylic ester based pressure-sensitive adhesives containing, as a major component, a polymer which contains a $C_{2-18}$ alkyl ester of (meth)acrylic acid as a first monomer. Examples of such an acrylic polymer include homopolymers of a (meth)acrylic alkyl ester and copolymers thereof. Herein, the alkyl in the (meth)acrylic alkyl ester is preferably a linear or branched $C_{4-12}$ alkyl. Specific examples of such a (meth)acrylic alkyl ester include butyl(meth)acrylate, t-butyl(meth)acrylate, pentyl(meth)acrylate, hexyl(meth)acrylate, heptyl(meth)acrylate, octyl(meth)acrylate, isooctyl(meth)acrylate, nonyl(meth)acrylate, isononyl(meth)acrylate, decyl(meth)acrylate, undecyl(meth)acrylate, dodecyl(meth)acrylate and 2-ethylhexyl(meth)acrylate.

The (meth)acrylic alkyl ester is preferably polymerized in a proportion of 50% by weight or more, and more preferably 60% by weight or more.

Further, the acrylic pressure-sensitive adhesive may contain a second monomer which is copolymerizable with the foregoing (meth)acrylic alkyl ester. Examples of such a monomer include monomers having a functional group capable of becoming a crosslinking point in using a crosslinking agent. Specific examples thereof include monomers having neither a carboxyl group nor a sulfonyl group, for example, hydroxyethyl(meth)acrylates (for example, 2-hydroxyethyl(meth)acrylate), hydroxypropyl(meth)acrylate, glycidyl(meth)acrylate and ethylene glycol diacrylate; and monomers having a carboxyl group, for example, (meth)acrylic acid, itaconic acid, maleic acid, mesaconic acid, citraconic acid and glutaconic acid. Such a second monomer can be used singly or in combination of two or more kinds thereof.

Furthermore, in addition to the second monomer, a third monomer may be contained, if desired. Such a third monomer can be used for the purposes of adjusting the cohesion of the pressure-sensitive adhesive layer and adjusting the solubility or release property of bisoprolol. Examples of the third monomer include vinyl esters, for example, vinyl acetate and vinyl propionate; vinyl ethers, for example, methyl vinyl ether and ethyl vinyl ether; vinyl amides, for example, N-vinyl-2-pyrrolidone and N-vinylcaprolactam; (meth)acrylic alkyl esters; amide group-containing monomers, for example, (meth)acrylamide and dimethyl(meth)acrylamide; alkoxyl group-containing monomers, for example, methoxyethyl(meth)acrylates (for example, 2-methoxyethyl acrylate) and ethoxyethyl(meth)acrylates; vinyl based monomers, for example, styrene, vinylpyridine, vinyl imidazole and vinyl morpholine; acrylamides, for example, methylolacrylamide and N,N-dimethylaminopropyl acrylamide; methoxynonaethylene glycol acrylate; acryloyl morpholine; and phenoxypolyethylene glycol(meth)acrylate. Such a third monomer can be used singly or in combination of two or more kinds thereof.

Of these acrylic pressure-sensitive adhesives, from the viewpoint the matter that the skin adhesion strength can be easily adjusted, those obtained by blending the first monomer (especially 2-ethylhexyl acrylate), the second monomer (especially acrylic acid) and the third monomer (especially N-vinyl-2-pyrrolidone) in a weight ratio of about 40 to 99.9/0.1 to 10/0 to 30 and copolymerizing them are preferable.

Also, according to the percutaneous administration device of the invention, the maximum value of release rate of bisoprolol is preferably obtained at a time during a period of from immediately after the application on skin until a lapse of 6 hours, more preferably until a lapse of 5 hours, and further preferably until a lapse of 4 hours. Although a measure for achieving this is not particularly limited, examples thereof include a measure in which an acrylic pressure-sensitive adhesive containing, as the foregoing second monomer, a monomer which is copolymerizable with the foregoing (meth)acrylic alkyl ester and which contains neither a carboxyl group nor a sulfonyl group, or a rubber based pressure-sensitive adhesive is employed as the pressure-sensitive adhesive. Although a mechanism for obtaining such an release profile from such a pressure-sensitive adhesive has not been elucidated yet, the present inventors suppose that an interaction between such a pressure-sensitive adhesive and bisoprolol contributes thereto. In such an acrylic pressure-sensitive adhesive, the copolymerizable monomer can be used singly or in combination of two or more kinds thereof.

Specific examples of the second monomer containing neither a carboxyl group nor a sulfonyl group include hydroxyethyl(meth)acrylates (for example, 2-hydroxyethyl methacrylate), hydroxypropyl(meth)acrylate and ethylene glycol diacrylate. Of these acrylic pressure-sensitive adhesives, from the viewpoint of the matter that the skin adhesion strength can be easily adjusted, for example, those obtained by blending the first monomer (especially 2-ethylhexyl acrylate), the second monomer (especially 2-methoxyethyl acrylate) and the third monomer (especially 2-hydroxyethyl methacrylate) in a weight ratio of about 40 to 90/0 to 50/1 to 20 and copolymerizing them are preferable.

If desired, such an acrylic pressure-sensitive adhesive may be subjected to a physical crosslinking treatment by means of irradiation with radiations, for example, irradiation with ultraviolet rays and irradiation with electron beams; or a chemical crosslinking treatment using various kinds of crosslinking agents, for example, isocyanate based compounds (for example, trifunctional isocyantes), organic peroxides, organometal salts, metal alcoholates, metal chelate compounds and polyfunctional compounds (for example, polyfunctional external crosslinking agents and polyfunctional internal crosslinking monomers such as diacrylates and dimethacrylates).

The rubber based pressure-sensitive adhesive is advantageous from the standpoints that the drug release property from the pressure-sensitive adhesive layer containing a rubber based pressure-sensitive adhesive is especially high; that it is easy to control the drug release; and that there is no possibility of residual monomers, and therefore, the drug stability is high. The content of the rubber based pressure-sensitive adhesive is preferably from 15 to 60% by weight, and more preferably from 15 to 55% by weight relative to the total weight of the pressure-sensitive adhesive layer.

The rubber based pressure-sensitive adhesive is not particularly limited, and examples thereof include rubber based pressure-sensitive adhesives containing, as a major component, at least one member selected among polyisobutylene, polyisoprene, butyl rubber and a styrene/diene/styrene copolymer. Of these, polyisobutylene is favorably used because it has high drug stability and is able to make both adhesion strength and cohesion compatible with each other. In that case, one kind of polyisobutylene may be contained singly, or two or more kinds of polyisobutylene having a different molecular weight may be contained.

In the case where one kind of polyisobutylene is contained singly, the content of polyisobutylene is preferably from 15 to 60% by weight, and more preferably from 15 to 55% by weight relative to the total weight of the pressure-sensitive adhesive layer. When the content of polyisobutylene is less than 15% by weight, there is a possibility that it is difficult to impart necessary internal cohesion to the pressure-sensitive adhesive layer, whereas when it exceeds 60% by weight, there is a possibility that the skin adhesiveness and tackiness of the pressure-sensitive adhesive layer are reduced.

Also, in the case where one kind of polyisobutylene is contained singly, although the molecular weight of polyisobutylene is not particularly limited, it is preferably from 40,000 to 5,500,000, and more preferably from 45,000 to 5,000,000 in terms of viscosity average molecular weight. When the viscosity average molecular weight is less than 40,000, there is a possibility that it is difficult to impart necessary internal cohesion to the pressure-sensitive adhesive layer, whereas when it exceeds 5,500,000, there is a possibility that the skin adhesiveness and tackiness of the pressure-sensitive adhesive layer are reduced.

In order to make both adequate cohesion of the pressure-sensitive adhesive layer and adequate flexibility and skin adhesiveness easily compatible with each other, it is preferable that two or more kinds of polyisobutylene having a different molecular weight are contained. The terms "two or more kinds of polyisobutylene having a different molecular weight" as referred to in the present specification refer to polyisobutylene having a peak of molecular weight distribution measured by gel permeation chromatography (GPC) in two or more independent regions. The molecular weight distribution of each polyisobutylene generally has a single peak. Accordingly, in the "two or more kinds of polyisobutylene having a different molecular weight", for example, two or more kinds of polyisobutylene having a different viscosity average molecular weight are contained. It is preferable that the polyisobutylene comprises, for example, a first polyisobutylene and a second polyisobutylene having a molecular weight relatively lower than that of the first polyisobutylene. The first polyisobutylene is able to impart adequate cohesion to the pressure-sensitive adhesive layer, and the second polyisobutylene is able to impart adequate flexibility and skin adhesiveness to the pressure-sensitive adhesive layer.

The molecular weight of each of the first polyisobutylene and the second polyisobutylene is not particularly limited. In order to obtain satisfactory adhesiveness and sufficient release property of bisoprolol, the viscosity average molecular weight of the first polyisobutylene is preferably from 1,800,000 to 5,500,000, and more preferably from 2,000,000 to 5,000,000, and the viscosity average molecular weight of the second polyisobutylene is preferably from 40,000 to 85,000, and more preferably from 45,000 to 65,000. When the viscosity average molecular weight of the first polyisobutylene is less than 1,800,000, there is a possibility that it is difficult to impart necessary internal cohesion to the pressure-sensitive adhesive layer, whereas when it exceeds 5,500,000, there is a possibility that the skin adhesiveness and tackiness of the pressure-sensitive adhesive layer are reduced. Further, when the viscosity average molecular weight of the second polyisobutylene is less than 40,000, there is a possibility that a sticky feeling reveals in the pressure-sensitive adhesive layer and that the skin surface is contaminated, whereas when it exceeds 85,000, there is a possibility that the skin adhesiveness and tackiness of the pressure-sensitive adhesive layer are reduced. As to each of the first polyisobutylene and the second polyisobutylene, two or more kinds thereof can be combined within the range of the molecular weight distribution thereof and used.

The viscosity average molecular weight as referred to in this specification is a value determined by calculating a Staudinger's index $(J_0)$ from a capillary flow time on an Ubbelohode viscometer at 20° C. according to the Suhulz-Blaschke equation and applying this $J_0$ value according to the following equation (2).

$$J_0 = \eta_{sp}/c(1+0.31\eta_{sp}) \text{ (cm}^3\text{/g) (Suhulz-Blaschke equation)} \quad (2)$$

$$\eta_{sp} = t/t_0 - 1$$

t: Flow time of the solution (according to the Hagenbach-Couette correction equation)

$t_0$: Flow time of the solvent (according to the Hagenbach-Couette correction equation)

c: Concentration of the solution (g/cm$^3$)

$$J_0 = 3.06 \times 10^{-2} Mv^{0.65}$$

Mv: Viscosity average molecular weight

In the case where the pressure-sensitive adhesive layer is constituted of two or more kinds of polyisobutylene having a different molecular weight, the total content of polyisobutylene is preferably from 15 to 60% by weight, and more preferably from 15 to 55% by weight relative to the total weight of the pressure-sensitive adhesive layer. When the total content of polyisobutylene is less than 15% by weight, there is a possibility that it is difficult to impart necessary internal cohesion to the pressure-sensitive adhesive layer, whereas when it exceeds 60% by weight, there is a possibility that the skin adhesiveness and tackiness of the pressure-sensitive adhesive layer are reduced.

Also, in the case where the polyisobutylene is constituted of two kinds of polyisobutylene having a different molecular weight, a blending proportion (a/b) of the first polyisobutylene (a) to the second polyisobutylene (b) is preferably from 1/0.1 to 1/3, more preferably from 1/0.1 to 1/2.5, and further preferably from 1/0.3 to 1/2 in terms of a weight ratio. As to these two kinds of polyisobutylene, when the blending proportion of the second polyisobutylene (b) exceeds the foregoing upper limit, there is a possibility that the reduction of internal cohesion of the pressure-sensitive adhesive layer becomes large, whereas it is less than the lower limit, there is a possibility that the reduction of skin adhesion strength of the pressure-sensitive adhesive layer becomes large.

In the case where a rubber based pressure-sensitive adhesive is used for the pressure-sensitive adhesive layer, as a tackifier, one which is known in the field of percutaneous administration device may be properly chosen and used. Examples of the tackifier include petroleum based resins (for example, aromatic petroleum resins and aliphatic petroleum resins), terpene based resins, rosin based resins, coumarone-indene resins, styrene based resins (for example, a styrene resin and an α-methylstyrene resin) and hydrogenated petroleum resins (for example, alicyclic saturated hydrocarbon resins). Of these, alicyclic saturated hydrocarbon resins are favorable because of satisfactory drug storage stability.

The tackifier can be used singly or in combination of two or more kinds thereof. In the case where the tackifier is used in combination of two or more kinds thereof, for example, resins having a different kind of resin or a different softening point may be combined.

The content of the tackifier is preferably from 15 to 55% by weight, and more preferably from 20 to 50% by weight relative to the total weight of the pressure-sensitive adhesive layer. When the content of the tackifier is less than 15% by weight, there may be the case where the tackiness and cohesion are poor, whereas when it exceeds 55% by weight, the pressure-sensitive adhesive becomes rigid, whereby the skin adhesiveness tends to be reduced.

Also, in the percutaneous administration device of the invention, bisoprolol to be contained in the percutaneous administration device is preferably availed to an extent of 65% by weight or more, more preferably 70% by weight or more, further preferably 75% by weight or more, and most preferably 80% by weight or more during a period of from immediately after the application on skin until a lapse of 24 hours. In the case where bisoprolol is most ideally availed, the availability is 100% by weight. The availability of bisoprolol during a period of from immediately after the application on skin until a lapse of 24 hours as referred to herein refers to a value determined according to the following equation (3).

$$\text{Availability of bisoprolol (\% by weight)} = p/q \times 100 \quad (3)$$

p: Accumulated release amount of bisoprolol during a period of from immediately after the application on skin until a lapse of 24 hours ($\mu g/cm^2$)

q: Weight of bisoprolol in the pressure-sensitive adhesive layer just before the application on skin ($\mu g/cm^2$)

As mentioned above, since the majority of bisoprolol contained in the percutaneous administration device is released until the time of peeling, the availability of drug is high, and bisoprolol in a liquid state substantially disappears in the preparation at the time of peeling. Therefore, there is brought an effect that the cohesion of the pressure-sensitive adhesive layer is enhanced to suppress the physical irritation at the time of peeling. That is, the percutaneous administration device of the invention according to an embodiment in which bisoprolol to be contained in the percutaneous administration device is availed to an extent of 65% by weight or more during a period of from immediately after the application on skin until a lapse of 24 hours is reduced with respect to not only the skin irritation by the drug, namely bisoprolol but the physical irritation to be caused due to a peeling operation. Therefore, the skin irritation at the time of peeling can be more effectively suppressed.

A measure for availing 65% by weight or more of bisoprolol contained in the percutaneous administration device during a period of from immediately after the application on skin until a lapse of 24 hours is not particularly limited, and examples thereof include a method in which the foregoing acrylic pressure-sensitive adhesive which contains neither a carboxyl group nor a sulfonyl group or the foregoing rubber based pressure-sensitive adhesive is employed, and an organic liquid component as described below is contained in the pressure-sensitive adhesive layer.

Furthermore, in the percutaneous administration device of the invention, it is preferable that an accumulated release amount of bisoprolol per unit area during a period of from immediately after the application on skin until a lapse of 12 hours is larger than an accumulated release amount of bisoprolol per unit area during a period of from a lapse of 12 hours until a lapse of 24 hours after the application on skin. In view of the matter that the accumulated release amount of bisoprolol per unit area is the total sum of the absolute amount of bisoprolol which has permeated through a human skin, it is strongly related to the skin irritation. Therefore, the accumulated release amount of bisoprolol during a period of from immediately after the application on skin until a lapse of 12 hours is preferably from 1.2 to 5 times, and more preferably from 1.5 to 4 times the accumulated release amount of bisoprolol during a period of from a lapse of 12 hours until a lapse of 24 hours after the application on skin.

In order to obtain such an accumulated release amount, it is necessary to strictly control the percutaneous administration device of the invention such that the drug release behavior from the pressure-sensitive adhesive layer is reduced with time. A method for achieving such a purpose is not particularly limited, and examples thereof include a method of controlling the diffusibility of bisoprolol in the pressure-sensitive adhesive layer. Examples of such a method include the addition of an organic liquid component in the pressure-sensitive adhesive layer.

That is, when an adequate amount of an organic liquid component is added in the pressure-sensitive adhesive layer, the diffusibility of bisoprolol in the pressure-sensitive adhesive layer is enhanced, whereby the concentration of bisoprolol in the pressure-sensitive adhesive can be reduced within a short period of time after start of the application. As a result, the foregoing accumulated release amount and availability are achieved.

The organic liquid component is not particularly limited so far as it is a liquid organic component to be added other than bisoprolol as the drug and is compatible with other constitutional components of the pressure-sensitive adhesive layer (for example, the pressure-sensitive adhesive and the tackifier). From the standpoint of greatly contributing to the acceleration of absorption of bisoprolol and the enhancement of solubility of bisoprolol into the pressure-sensitive adhesive layer, fatty acid alkyl esters and long-chain alcohols are favorably used as the organic liquid component. The organic liquid component may be used singly or in combination of two or more kinds thereof.

Examples of the fatty acid alkyl ester include fatty acid alkyl esters composed of a higher fatty acid having from 12 to 16 carbon atoms, and preferably from 12 to 14 carbon atoms and a lower monohydric alcohol having from 1 to 4 carbon atoms. The higher fatty acid is preferably lauric acid (C12), myristic acid (C14) or palmitic acid (C16), and more preferably myristic acid. Examples of the monohydric alcohol include methyl alcohol, ethyl alcohol, propyl alcohol, isopropyl alcohol and butyl alcohol, with isopropyl alcohol being preferable. Accordingly, the fatty acid alkyl ester is most preferably isopropyl myristate, and by using this compound, the acceleration of absorption and the enhancement of solubility of bisoprolol and the drug availability can be achieved at high levels.

Furthermore, examples of the long-chain alcohol include saturated or unsaturated alcohols having from 12 to 28 carbon atoms, and preferably from 12 to 24 carbon atoms. From the standpoint of storage stability, saturated alcohols are favorably used as the long-chain alcohol. Further, examples of the long-chain alcohol include linear or branched alcohols, and these alcohols can be used in admixture. Examples of the linear alcohol include 1-dodecanol, 1-tetradecanol, 1-hexadecanol and stearyl alcohol. Of these, 1-dodecanol is preferable because it is excellent in the compatibility with polyisobutylene and the stability of bisoprolol. In the case where the compatibility with polyisobutylene is hardly obtainable, branched alcohols having from 16 to 28 carbon atoms, and preferably from 18 to 24 carbon atoms can be used. Specific examples thereof include 2-hexyldecanol, isostearyl alcohol, 2-octyldodecanol and 2-decyltetradecanol. Of these, 2-octyldodecanol is preferable because it is excellent in the compatibility with polyisobutylene and is able to enhance the solubility of bisoprolol.

Even when the fatty acid alkyl ester is used singly as the organic liquid component, the foregoing effects are thoroughly obtainable. However, the use of a combination of the fatty acid alkyl ester and the long-chain alcohol is preferable because not only the permeability and solubility of bisoprolol but the skin adhesiveness of the pressure-sensitive adhesive layer are more enhanced. A blending proportion (c/d) of the fatty acid alkyl ester (c) to the long-chain alcohol (d) is preferably from 1/0 to 1/0.5, more preferably from 1/0 to 1/0.4, and further preferably from 1/0.05 to 1/0.4 in terms of a weight ratio. When the blending proportion of the long-chain alcohol (d) in these two kinds of organic liquid components exceeds the foregoing upper limit, since the proportion of the fatty acid alkyl ester (c) is relatively reduced, there is a possibility that it is difficult to sustain the acceleration of absorption at high levels.

As described above, in many cases, the organic liquid component effectively acts as a permeation accelerator. On that occasion, by increasing the content of the organic liquid component, the skin permeability is enhanced. That is, by containing a large amount of the organic liquid component in the pressure-sensitive adhesive layer, the skin permeability becomes higher, and a composition in which the skin permeability is easily controllable is revealed. Therefore, it can be said that this composition is an ideal composition of pressure-sensitive adhesive as the percutaneous administration device. Further, by containing the organic liquid component in the pressure-sensitive adhesive layer, it is possible to impart adequate flexibility and skin adhesiveness to the pressure-sensitive adhesive layer.

The content of the organic liquid component is preferably from 20 to 40% by weight, and more preferably from 25 to 38% by weight relative to the total weight of the pressure-sensitive adhesive layer. When the content of the organic liquid component is less than 20% by weight, there may be the case where bleeding of the drug from the pressure-sensitive adhesive layer is generated. As a result, there is a possibility that the adhesiveness is reduced and that it is difficult to obtain sufficient skin permeability. Furthermore, when the content of the organic liquid component exceeds 40% by weight, there may be the case where the cohesion of the pressure-sensitive adhesive layer is largely reduced, and there is a possibility that cohesive failure is generated.

In the percutaneous administration device of the invention, other components than the foregoing may be properly added.

For example, for the purpose of further increasing the solubility of the drug in the pressure-sensitive adhesive layer to obtain more satisfactory low skin irritation, a dissolution aid composed of other liquid organic component that the foregoing can be blended in the pressure-sensitive adhesive layer as the need arises. As the dissolution aid, materials which are excellent in the compatibility with the pressure-sensitive adhesive, are able to thoroughly dissolve the drug therein, are small in a possibility of bleeding of bisoprolol from the pressure-sensitive adhesive layer and do not adversely affect the pressure-sensitive adhesive characteristic and drug emission properties may be used. Specific examples thereof include esters of an organic acid (for example, fatty acids (for example, oleic acid, myristic acid and capric acid) and dicarboxylic acids (for example, adipic acid and sebacic acid)) and an alcohol (for example, ethanol and 2-propanol); polyhydric alcohols (for example, glycerin and propylene glycol) and di- or triesters thereof; esters of a polyhydric alcohol and an organic acid (for example, triacetin); and polyethers (for example, polyethylene glycol, polypropylene glycol and polyoxyethylene hydrogenated castor oil), as well as crotamiton.

Further, in order to enhance the cohesion, an adequate filler can be contained in the pressure-sensitive adhesive layer, if desired. Such a filler is not particularly limited, and examples thereof include inorganic fine particles such as silica, titanium oxide, zinc oxide, magnesium oxide, iron oxide, aluminum hydroxide, talc, kaolin, bentonite, barium sulfate and calcium carbonate; organic fine particles such as lactose, carbon black, polyvinylpyrrolidone, polyesters, polyolefins, polyurethanes, polyamides, celluloses and acrylic resins; and fibers such as polyesters, polyolefins, polyurethanes, polyamides, celluloses, acrylic resins and glass.

Furthermore, in the case of enhancing the skin adhesion strength, tackiness and flexibility, if desired, by containing an adequate softener in the pressure-sensitive adhesive layer, it is possible to impart adequate skin adhesion strength or tackiness to the pressure-sensitive adhesive layer. Such a softener is not particularly limited, and examples thereof include liquid rubbers such as liquid polybutene and liquid polyisoprene and organic liquid components such as liquid hydrocarbons (for example, liquid paraffin, squalane and squalene). Moreover, if desired, the adhesiveness to a skin may be reinforced by applying a cover tape or the like so as to cover a part or the whole of the percutaneous administration device of the invention, thereby reinforcing the skin adhesion.

In the invention, in the case of using the first polyisobutylene in the pressure-sensitive adhesive layer, a large amount of the organic liquid component can be contained, and as a result, sufficient absorption accelerating effect and solubility enhancing effect of the drug due to the organic liquid component can be obtained. According to this, it is possible to provide a percutaneous administration device which is able to suppress the reduction of cohesion and which is free from adhesive transfer and the like. Furthermore, with respect to the tackifier, by using a tackifier having a higher softening point within the foregoing temperature range, it is possible to achieve not only an enhancement of the cohesion but an enhancement of the skin adhesiveness at the same time. The thickness of the pressure-sensitive adhesive layer is usually from 30 to 300 µm, and preferably from 60 to 250 µm.

Although the backing is not particularly limited, those which are substantially impermeable against the drug or the like, namely those which are free from a reduction of the content to be caused due to the matter that bisoprolol as the active component and additives and the like in the pressure-sensitive adhesive layer pass therethrough and are lost from the back surface thereof, are preferable. As the backing, for example, single films made of a polyester, a polyamide, polyvinylidene chloride, polyethylene, polypropylene, polyvinyl chloride, an ethylene/ethyl acrylate copolymer, polytetrafluoroethylene, an ionomer resin, a metal foil, etc., or laminated films thereof can be used. Above all, for the purpose of making the adhesiveness (anchoring properties) between the backing and the pressure-sensitive adhesive layer satisfactory, it is preferable that the backing is formed of a laminated film of a nonporous plastic film and a porous film made of the foregoing materials. In that case, it is desirable that the pressure-sensitive adhesive layer is formed on the porous film side.

As such a porous film, those capable of enhancing the anchoring properties with the pressure-sensitive adhesive layers are employed. Specific examples thereof include papers, woven fabrics, non-woven fabrics, knitted fabrics and sheets having been subjected to a mechanical perforation treatment. Of these, papers, woven fabrics and non-woven fabrics are especially preferable from the viewpoints of handling properties and the like. As the porous film, one having a thickness in the range of from 10 to 200 µm is employed from the standpoints of an enhancement of anchoring properties, flexibility of the whole of the percutaneous administration device, application operability and the like. In the case of a thin percutaneous administration device such as a plaster type and a pressure-sensitive adhesive tape type, one having a thickness in the range of from 10 to 100 μm is employed.

Further, in the case where a woven fabric or a non-woven fabric is used as the porous film, its basis weight is preferably from 5 to 30 g/m$^2$, and more preferably from 6 to 15 g/m$^2$. As the most favorable backing, a laminated film of a polyester film (preferably a polyethylene terephthalate film) having a thickness of from 1.5 to 6 μm and a non-woven fabric made of a polyester (preferably polyethylene terephthalate) having a basis weight of from 6 to 15 g/m$^2$ is exemplified.

In the percutaneous administration device of the invention, for the purpose of protecting the pressure-sensitive adhesive surface of the pressure-sensitive adhesive layer until the time of use, it is desirable that a peel-off liner is laminated on the pressure-sensitive adhesive surface. The peel-off liner is not particularly limited so far as it can be subjected to a peel-off treatment and is able to secure a sufficiently light peeling force, and the examples of the peel-off liner include films such as polyesters, polyvinyl chloride, polyvinylidene chloride and polyethylene terephthalate, papers such as high-quality papers and glassine papers or film of polyolefin laminated with high quality paper or glassine paper, to which peel-off treatment is made by applying silicone resin or fluororesin on the surface contacting with the pressure-sensitive adhesive layer. The thickness of the peel-off liner is preferably from 10 to 200 μm, and more preferably from 25 to 100 μm.

As the peel-off liner, one made of a polyester (especially polyethylene terephthalate) resin is preferable from the standpoints of barrier properties, costs and the like. Furthermore, in that case, one having a thickness of from about 25 to 100 μm is preferable from the standpoint of handling properties.

The shape of the percutaneous administration device of the invention is not particularly limited, and examples thereof include a tape shape and a sheet shape.

The percutaneous administration device of the invention can be, for example, manufactured by dissolving a pressure-sensitive adhesive composition containing a pressure-sensitive adhesive and bisoprolol and optionally a tackifier and an organic liquid component in an adequate solvent such as toluene, coating the obtained solution on a peel-off liner and drying it to form a pressure-sensitive adhesive layer and then laminating a backing on the pressure-sensitive adhesive layer. Further, the percutaneous administration device of the invention can be, for example, manufactured by directly coating the foregoing pressure-sensitive adhesive solution on a backing and drying it to form a pressure-sensitive adhesive layer on the backing. In this operation, when the pressure-sensitive adhesive layer is formed by thickly applying a pressure-sensitive adhesive solution at a time, it becomes difficult to dry evenly in some cases; so, it is appropriate to repeat the applying operation twice or more to give a pressure-sensitive adhesive layer with sufficient thickness.

It is preferable that the percutaneous administration device of the invention is preserved or transported in a form of sealed package just before use. Packaging may be made, for example, by packing a single sheet of percutaneous administration device or several sheets of piled percutaneous administration devices with a wrapping material and then tightly closing the periphery with a heat seal. The wrapping material includes, for example, a sheet-form or film-form material, for which there is no particular limitation. In this case, a material allowing heat sealing is desirous in view of easiness of packaging or air-tightness. Such a packaging material includes, specifically and preferably, those using a heat-sealable plastic sheet such as polyethylene, ionomer resin, ethylene-vinyl acetate copolymer, ethylene-vinyl alcohol copolymer, polyacrylonitrile type copolymer, polyvinyl alcohol type copolymer, and the like. In particular, in order to prevent the contamination or oxidation of an active ingredient bisoprolol contained in the percutaneous administration device by contact with ambient air, it is preferred to use a laminated gas-impermeable film such as polyester film or metal foil. The packaging material is used in thickness of 10 to 200 μm. It is more preferable to use a high barrier polyacrylonitrile type copolymer as a lining material in the most inner layer of the above packaging material. Further, it is appropriate to think out a packaging form formed by embossing of the packaging material, dry edge processing (slightly enlarging the above liner portion compared to the percutaneous administration device) or blister molding processing (making the contact area small), since it is feared that handling of the package such as taking-out from the package becomes worse when the pressure-sensitive adhesive ingredient is leaked out from the side of the percutaneous administration device.

The percutaneous administration device of the invention may be taken out from the package, for example by tearing the above package, just before use, and the peel-off liner is peeled off, and the exposed pressure-sensitive adhesive surface is applied to the skin.

The directions for use of the percutaneous administration device of the invention vary with age, weight, condition and the like of a patient.

In the invention, the area of the percutaneous administration device can be considered for the purpose of achieving the administration of an effective amount of bisoprolol while applying the foregoing maximum value of the human skin permeation rate of bisoprolol. The area of the percutaneous administration device is preferably from 15 to 50 cm$^2$, more preferably from 18 to 48 cm$^2$, and further preferably from 20 to 45 cm$^2$. When the area of the percutaneous administration device is smaller than 15 cm$^2$, there is a possibility that it is difficult to administer an effective amount of bisoprolol while suppressing the skin irritation, whereas when it is larger than 50 cm$^2$, there is a possibility that the application operation is difficult and that stress is given to a patient during the application. In the case where strong medicinal properties are required, two or more sheets of the percutaneous administration device can be applied at the same time.

Although the administration frequency is not particularly limited, it is preferable that the percutaneous administration device is applied to a skin approximately once a day or two days. It is more preferable that the percutaneous administration device is applied once a day because the blood pressure can be controlled in conformity with a human life cycle.

Furthermore, the invention is concerned with an acting method of a percutaneous administration device of bisoprolol comprising a backing having on one surface thereof a pressure-sensitive adhesive layer containing bisoprolol, wherein a maximum value of a release rate of bisoprolol during a period of from immediately after the application on skin until a lapse of 24 hours is 30 μg/cm$^2$/hr or less; and a release rate of bisoprolol at the time of a lapse of 24 hours after the application on skin is 10 μg/cm$^2$/hr or less. The technical measures with respect to the above-described device can also be applied to this method.

EXAMPLES

The invention is hereunder specifically described with reference to the following Examples, but it should not be construed that the invention is limited to these Examples. Abbreviations used in the following Examples are as follows.

BSP: Bisoprolol
PIB1: Polyisobutylene having a viscosity average molecular weight of 4,000,000
PIB2: Polyisobutylene having a viscosity average molecular weight of 55,000
TF1: Tackifier, hydrogenated terpene based resin, softening point: 150° C.
TF2: Tackifier, alicyclic saturated hydrocarbon resin, softening point: 125° C.
IPM: Isopropyl myristate
ODO: 2-Octyldodecanol Examples 1 to 2

A viscous toluene solution of a pressure-sensitive adhesive composition was prepared according to a blending proportion shown in Table 1; the obtained solution was coated in a thickness after drying of 80 μm on a liner made of polyethylene terephthalate (PET) (thickness: 75 μm) which had been subjected to a silicone peel-off treatment; and this was then dried at 100° C. for 5 minutes in a hot air circulation type dryer, thereby forming a pressure-sensitive adhesive layer. This pressure-sensitive adhesive layer was stuck on a PET film having a thickness of 12 μm or a laminated film of a PET film having a thickness of 2 μm and a PET non-woven fabric of 12 g/m² on the non-woven fabric side, thereby obtaining a laminate in a sheet form. The PET-made liner of this laminate was peeled off, and several layers of a pressure-sensitive adhesive layer having the same composition and thickness as those described above were laminated on the exposed pressure-sensitive adhesive surface, thereby obtaining a percutaneous administration device provided with a pressure-sensitive adhesive layer having a thickness shown in Table 1. The blending amount of each of the components shown in Table 1 is a proportion (% by weight) on the basis of the total weight of the pressure-sensitive adhesive composition.

Example 3 and Comparative Examples 1 to 3

In an inert gas atmosphere, 70 parts by weight of 2-ethylhexyl acrylate, 20 parts by weight of 2-methoxyethyl acrylate, 10 parts by weight of 2-hydroxyethyl acrylate and 0.2 parts by weight of azobisisobutyronitrile were subjected to solution polymerization in ethyl acetate at 60° C., thereby preparing a solution of an acrylic pressure-sensitive adhesive. This acrylic pressure-sensitive adhesive, isopropyl myristate and bisoprolol were uniformly mixed and stirred in a vessel according to a blending proportion shown in Table 1; 0.6% by weight (relative to the solids of the pressure-sensitive adhesive) of ethyl acetoacetate aluminum diisopropylate was added; and the viscosity was adjusted with ethyl acetate. The obtained solution was coated in a thickness after drying as shown in Table 1 on a liner made of polyethylene terephthalate (PET) (thickness: 75 μm) which had been subjected to a silicone peel-off treatment; and this was dried at 100° C. for 5 minutes in a hot air circulation type dryer, thereby forming a pressure-sensitive adhesive layer. This pressure-sensitive adhesive layer was stuck on a PET film having a thickness of 12 μm or a laminated film of a PET film having a thickness of 2 μm and a PET non-woven fabric of 12 g/m² on the non-woven fabric side, followed by heat treating at 70° C. for 48 hours to obtain a percutaneous administration device in a sheet form.

TABLE 1

| | BSP | Acrylic pressure-sensitive adhesive | Polyisobutylene First | | Second | | Tackifier | Fatty acid ester | | Long-chain alcohol | | Thickness of pressure-sensitive adhesive layer (μm) | BSP content (mg/cm²) |
|---|---|---|---|---|---|---|---|---|---|---|---|---|---|
| Example 1 | 2 | — | PIB1 | 18 | PIB2 | 22 | TF1 30 | IPM | 23 | ODO | 5 | 160 | 0.32 |
| Example 2 | 1.4 | — | PIB1 | 18 | PIB2 | 20.6 | TF2 30 | IPM | 30 | — | — | 160 | 0.22 |
| Example 3 | 5 | 55 | — | — | — | — | — | IPM | 40 | — | — | 80 | 0.4 |
| Comparative Example 1 | 10 | 50 | — | — | — | — | — | IPM | 40 | — | — | 80 | 0.8 |
| Comparative Example 2 | 10 | 50 | — | — | — | — | — | IPM | 40 | — | — | 40 | 0.4 |
| Comparative Example 3 | 10 | 80 | — | — | — | — | — | IPM | 10 | — | — | 150 | 1.5 |

Figure 2:
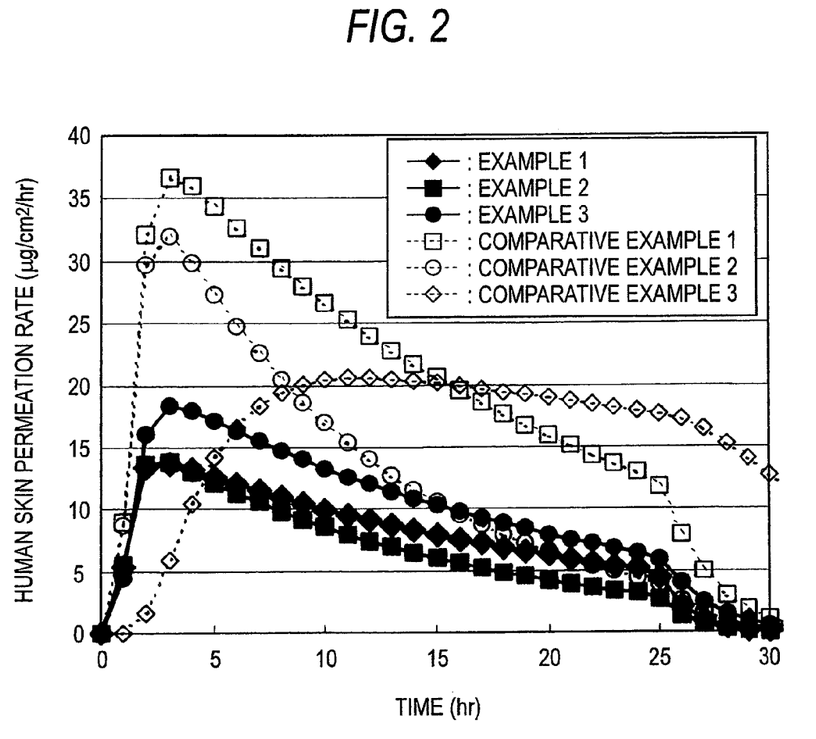
FIG. 2 is a graph showing a release rate (human skin permeation rate) of bisoprolol of the percutaneous administration device of bisoprolol obtained in each of the Examples and Comparative Examples.
Figure 3:
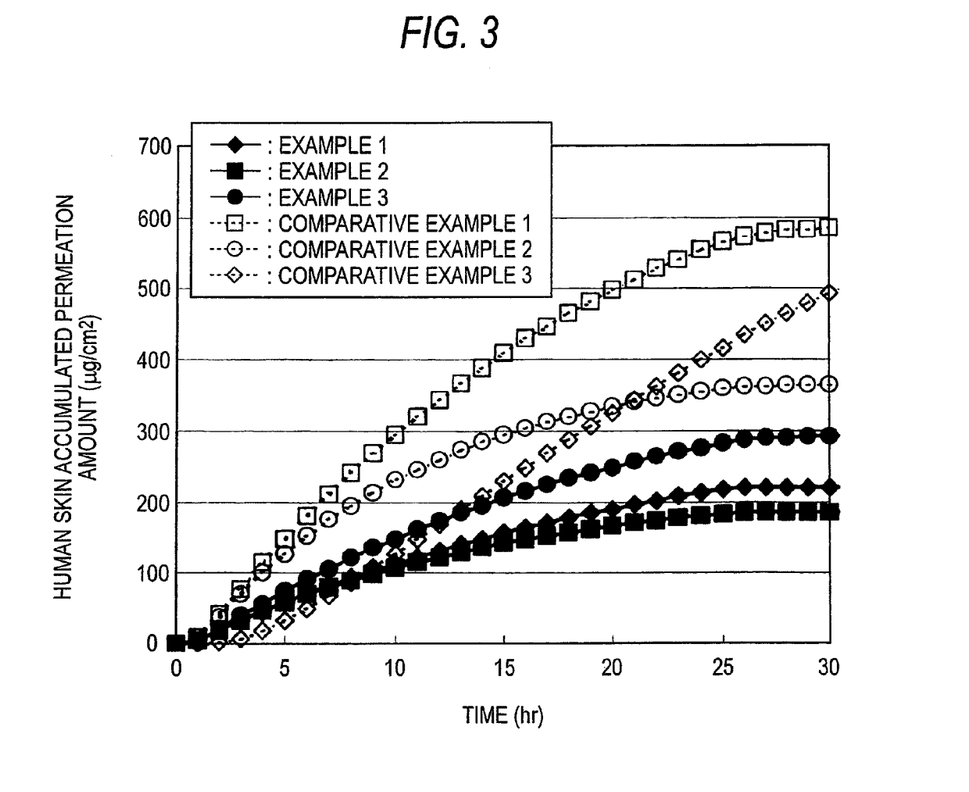
FIG. 3 is a graph showing an accumulated release amount (human skin accumulated permeation amount) of bisoprolol of the percutaneous administration device of bisoprolol obtained in each of the Examples and Comparative Examples.

Permeability of a skin removed from the back of a hairless mouse was tested by using the percutaneous administration device obtained in each of the Examples and Comparative Examples (backing: a laminated film of a PET film having a thickness of 2 μm and a PET non-woven fabric of 12 g/m²), and human skin permeability of bisoprolol was calculated. The calculation results are shown in Table 2. Furthermore, a release rate (human skin permeation rate) of bisoprolol of the percutaneous administration device of bisoprolol obtained in each of the Examples and Comparative Examples is shown in FIG. 2; and an accumulated release amount (human skin accumulated permeation amount) of bisoprolol is shown in FIG. 3.

<Test Method>

Each of the foregoing percutaneous administration devices which had been cut into a circular shape having a diameter of 16 mmφ was applied on a horny layer of a skin removed from the back of a hairless mouse (intact skin); the dermal side was installed in a Franz's type diffusion cell; and the test was carried out by using a phosphate buffered physiological saline (pH: 7.4) as a receptor solution at 32° C. The receptor solution was sampled at intervals of a certain time, and the amount of bisoprolol in the sampling solution was quantitatively determined by the HPLC method. The same test was carried out with respect to a skin obtained by stripping off a horny layer of a skin removed from the back of a hairless mouse by using a cellophane adhesive tape (stripped skin) Furthermore, a water elution test at 32° C. was carried out with respect to each of the Examples and Comparative Examples, and a diffusion coefficient of bisoprolol in the pressure-sensitive adhesive layer was calculated from the elution amount of bisoprolol from the percutaneous administration device according to the Higuchi's equation. The human skin permeability was calculated by a percutaneous absorption prediction system (SKIN-CAD™ Professional Edition ver. 5.0.1, available from i-Hive Communication Inc.) on the basis of the foregoing experimental results and the following parameters.

<Parameters>

Thickness of horny layer of skin of the back of hairless mouse: 10 μm

Total thickness of skin of the back of hairless mouse: Measured value

Thickness of horny layer of human skin: 20 μm

Total thickness of human skin: 500 μm

<Evaluation Score>

0: Redness was equal to that in the placebo tape.

1: Redness was slightly observed as compared with the placebo tape.

2: Redness was lightly observed as compared with the placebo tape.

3: Redness was distinctly observed as compared with the placebo tape.

4: Redness was observed to a medium extent as compared with the placebo tape.

5: Redness was strongly observed as compared with the placebo tape.

TABLE 2

| | Time with maximum of skin permeation rate (hr) | Skin permeation rate ($\mu g/cm^2/hr$) | | Ratio of accumulated permeation amount (0 to 12 hr)/(12 to 24 hr) | Availability of drug (%) | Inclination of reduction of release rate |
|---|---|---|---|---|---|---|
| | | Maximum value | 24 hr | | | |
| Example 1 | 2.0 | 13.7 | 5.2 | 1.6 | 67 | 0.39 |
| Example 2 | 1.9 | 13.8 | 3.2 | 2.1 | 82 | 0.48 |
| Example 3 | 2.2 | 18.4 | 6.5 | 1.6 | 69 | 0.55 |
| Comparative Example 1 | 2.6 | 36.7 | 13.0 | 2.7 | 69 | 1.11 |
| Comparative Example 2 | 2.2 | 32.0 | 4.4 | 2.7 | 89 | 1.27 |
| Comparative Example 3 | 10.9 | 20.6 | 17.9 | 0.7 | 27 | 0.21 |

It was noted that the release rate of bisoprolol is gently reduced after it had arrived at the maximum value in the Examples, whereas the release rate of bisoprolol was abruptly reduced in the Comparative Examples 1 and 2. On the other hand, in the Comparative Example 3, although the release rate of bisoprolol is gently reduced after it had arrived at the maximum value, the value at the time of a lapse of 24 hours is high (see FIG. 2). In the light of the above, in the Examples, a large fluctuation of the release rate of bisoprolol is suppressed, whereby the concentration of bisoprolol in blood becomes stable, and therefore, it is effective to persistently administer a therapeutically or preventively effective amount of bisoprolol into a living body.

In addition, in the Examples, the accumulated release amount of bisoprolol during a period of from immediately after the application on skin until a lapse of 12 hours was larger than the accumulated administration amount of bisoprolol during a period of from a lapse of 12 hours until a lapse of 24 hours after the application on skin. Furthermore, it was noted that in all of the Examples, the availability of bisoprolol was high as 65% or more.

A rabbit skin irritation test (n=3) was carried out by using the percutaneous administration devices obtained in each of the Examples and Comparative Examples (backing: a PET film having a thickness of 12 μm). A placebo tape corresponding to each of the Examples and Comparative Examples was prepared in a sample size of 16 mmϕ in the same manner as in the Examples and Comparative Examples and applied adjacent to the percutaneous administration device of each of the Examples and Comparative Examples. Each of them was applied on a healthy skin for 24 hours on the basis of the following evaluation score, and a change of redness with time during the application was evaluated while comparing with the placebo tape. Average values of the test results are shown in Table 3.

TABLE 3

| | Application time | | | | | | | | |
|---|---|---|---|---|---|---|---|---|---|
| | 0 hr | 1 hr | 2 hr | 3 hr | 4 hr | 6 hr | 9 hr | 12 hr | 24 hr |
| Example 1 | 0.0 | 0.3 | 1.3 | 2.0 | 1.7 | 0.3 | 0.0 | 0.0 | 0.0 |
| Example 2 | 0.0 | 1.0 | 1.7 | 2.0 | 1.3 | 0.7 | 0.0 | 0.0 | 0.0 |
| Example 3 | 0.0 | 0.7 | 1.7 | 2.0 | 1.7 | 0.7 | 0.0 | 0.0 | 0.0 |
| Comparative Example 1 | 0.0 | 1.0 | 1.3 | 2.7 | 2.3 | 2.0 | 1.3 | 1.0 | 0.3 |
| Comparative Example 2 | 0.0 | 1.0 | 1.7 | 2.3 | 1.7 | 1.0 | 1.0 | 0.7 | 0.3 |
| Comparative Example 3 | 0.0 | 0.3 | 1.0 | 2.0 | 2.0 | 2.0 | 2.0 | 2.0 | 2.0 |

In all of the percutaneous administration devices of the Examples and Comparative Examples, redness was observed from the beginning of application. However, in the Examples, the redness disappeared since a lapse of 9 hours after the application on skin and was substantially at the same degree as the begging of application. In the Comparative Examples, redness was observed even upon a lapse of 24 hours after the application.

In the light of the above, in the percutaneous administration devices of the Examples, there was observed a tendency that the skin irritation was rapidly reduced until a lapse of 24 hours after the application on skin.

While the invention has been described in detail and with reference to specific embodiments thereof, it will be apparent to one skilled in the art that various changes and modifications can be made therein without departing from the spirit and scope thereof.

The present application is based on Japanese Patent Application No. 2007-059279 filed on Mar. 8, 2007, and the contents are incorporated herein by reference.

INDUSTRIAL APPLICABILITY

According to the present invention, it is possible to provide a percutaneous administration device in which the skin irritation during the application, especially at the time of peeling is reduced and by which a therapeutically or preventively effective amount of bisoprolol can be persistently administered into a living body.

The invention claimed is:

1. A transdermal device for the administration of bisoprolol, the transdermal device comprising:
   a backing; and
   a pressure-sensitive adhesive layer laminated on one side of the backing, the pressure-sensitive adhesive layer comprising:
      bisoprolol free base, wherein the concentration of bisoprolol free base is 0.5% to 5% by weight of the pressure-sensitive adhesive layer;
      at least two species of pressure-sensitive adhesive, wherein the first species of pressure-sensitive adhesive is a first polyisobutylene having a viscosity average molecular weight of from 2,000,000 to 5,000,000, wherein the second species of pressure-sensitive adhesive is a second polyisobutylene having a viscosity average molecular weight of from 45,000 to 65,000, wherein the proportion of first polyisobutylene to second polyisobutylene in the pressure-sensitive adhesive layer is in the ratio range of from 1:0.3 to 1:2 by weight, and wherein all the species of pressure-sensitive adhesive in the pressure-sensitive adhesive layer are polyisobutylenes and the total concentration of polyisobutylenes in the pressure-sensitive adhesive layer is 15% to 55% by weight of the pressure-sensitive adhesive layer;
      isopropyl myristate, wherein the concentration of isopropyl myristate is 20% to 40% by weight of the pressure-sensitive adhesive layer; and
      tackifier, wherein the concentration of tackifier is 20% to 50% by weight of the pressure-sensitive adhesive layer; and
   wherein the thickness of the pressure-sensitive adhesive layer is 60 μm to 250 μm;
   wherein the amount of bisoprolol free base per unit area of the pressure-sensitive adhesive layer is from 0.1 to 0.5 mg/cm$^2$; and
   wherein the release rate of bisoprolol free base from the pressure-sensitive adhesive layer does not exceed 20 μg/cm$^2$/hr during the 24-hour time period immediately following initial application of the transdermal device to the skin.

2. The transdermal device of claim 1, wherein the viscosity average molecular weight of the first polyisobutylene is 4,000,000.

3. The transdermal device of claim 2, wherein the viscosity average molecular weight of the second polyisobutylene is 55,000.

4. The transdermal device of claim 1, wherein the concentration of the first polyisobutylene is 18% by weight of the pressure-sensitive adhesive layer.

5. The transdermal device of claim 4, wherein the concentration of the second polyisobutylene is 22% by weight of the pressure-sensitive adhesive layer.

6. The transdermal device of claim 4, wherein the concentration of the second polyisobutylene is 20.6% by weight of the pressure-sensitive adhesive layer.

7. The transdermal device of claim 2, wherein the concentration of the first polyisobutylene is 18% by weight of the pressure-sensitive adhesive layer.

8. The transdermal device of claim 1, wherein the tackifier is selected from the group consisting of alicyclic saturated hydrocarbon resin, hydrogenated terpene-based resin, and combinations thereof.

9. The transdermal device of claim 1, wherein the pressure-sensitive adhesive layer further comprises a branched alcohol having from 18 to 24 carbon atoms, and wherein the total concentration, in the pressure-sensitive adhesive layer, of isopropyl myristate and all species of alcohol having from 12 to 28 carbon atoms is 25% to 40% by weight of the pressure-sensitive adhesive layer.

10. The transdermal device of claim 9, wherein the branched alcohol having from 18 to 24 carbon atoms is selected from the group consisting of 2-hexyldecanol, isostearyl alcohol, and 2-decyltetradecanol.

11. The transdermal device of claim 9, wherein the branched alcohol having from 18 to 24 carbon atoms is 2-octyldodecanol.

12. A transdermal device for the administration of bisoprolol, the transdermal device comprising:
   a backing; and
   a pressure-sensitive adhesive layer laminated on one side of the backing, the pressure-sensitive adhesive layer comprising:
      bisoprolol free base, wherein the concentration of bisoprolol free base is 0.5% to 5% by weight of the pressure-sensitive adhesive layer;
      at least two species of pressure-sensitive adhesive, wherein the first species of pressure-sensitive adhesive is a first polyisobutylene having a viscosity average molecular weight of from 2,000,000 to 5,000,000, wherein the second species of pressure-sensitive adhesive is a second polyisobutylene having a viscosity average molecular weight of from 45,000 to 65,000, wherein the proportion of first polyisobutylene to second polyisobutylene in the pressure-sensitive adhesive layer is in the ratio range of from 1:0.3 to 1:2 by weight, and wherein all the species of pressure-sensitive adhesive in the pressure-sensitive adhesive layer are polyisobutylenes and the total concentration of polyisobutylenes in the pressure-sensitive adhesive layer is 15% to 55% by weight of the pressure-sensitive adhesive layer;
      isopropyl myristate;
      a branched alcohol having from 18 to 24 carbon atoms selected from the group consisting of 2-hexyldecanol, isostearyl alcohol, 2-octyldodecanol, 2-decyltetradecanol, and combinations thereof; and
      tackifier, wherein the concentration of tackifier is 20% to 50% by weight of the pressure-sensitive adhesive layer; and
   wherein the proportion of isopropyl myristate to the branched alcohol having from 18 to 24 carbon atoms is in the ratio range of from 1:0.05 to 1:0.4 by weight;
   wherein the total concentration, in the pressure-sensitive adhesive layer, of isopropyl myristate and all species of alcohol having from 12 to 28 carbon atoms is 20% to 40% by weight of the pressure-sensitive adhesive layer;
   wherein the thickness of the pressure-sensitive adhesive layer is 60 μm to 250 μm;
   wherein the amount of bisoprolol free base per unit area of the pressure-sensitive adhesive layer is from 0.1 to 0.5 mg/cm$^2$; and wherein the release rate of bisoprolol free base from the pressure-sensitive adhesive layer does not exceed 20 µg/cm$^2$/hr during the 24-hour time period immediately following initial application of the transdermal device to the skin.

13. The transdermal device of claim 12, wherein the viscosity average molecular weight of the first polyisobutylene is 4,000,000.

14. The transdermal device of claim 13, wherein the viscosity average molecular weight of the second polyisobutylene is 55,000.

15. The transdermal device of claim 12, wherein the concentration of the first polyisobutylene is 18% by weight of the pressure-sensitive adhesive layer.

16. The transdermal device of claim 12, wherein the branched alcohol having from 18 to 24 carbon atoms is 2-octyldodecanol.

17. The transdermal device of claim 13, wherein the branched alcohol having from 18 to 24 carbon atoms is 2-octyldodecanol.

18. The transdermal device of claim 16, wherein the concentration of isopropyl myristate is 23% by weight of the pressure-sensitive adhesive layer and the concentration of 2-octyldodecanol is 5% by weight of the pressure-sensitive adhesive layer.

* * * * *